United States Patent
Eggers

(10) Patent No.: US 9,753,109 B2
(45) Date of Patent: Sep. 5, 2017

(54) MAGNETIC RESONANCE IMAGING OF CHEMICAL SPECIES WITH A SPECTRAL MODEL

(75) Inventor: Holger Eggers, Ellerhoop (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1314 days.

(21) Appl. No.: 13/577,266

(22) PCT Filed: Feb. 16, 2011

(86) PCT No.: PCT/IB2011/050639
§ 371 (c)(1),
(2), (4) Date: Aug. 6, 2012

(87) PCT Pub. No.: WO2011/101786
PCT Pub. Date: Aug. 25, 2011

(65) Prior Publication Data
US 2012/0316795 A1    Dec. 13, 2012

(30) Foreign Application Priority Data
Feb. 22, 2010    (EP) .................................... 10154202

(51) Int. Cl.
G01R 33/48    (2006.01)
G01R 33/561    (2006.01)
G01N 24/08    (2006.01)

(52) U.S. Cl.
CPC .......... *G01R 33/4828* (2013.01); *G01N 24/08* (2013.01); *G01N 24/088* (2013.01); *G01R 33/5615* (2013.01)

(58) Field of Classification Search
CPC .................. G01R 33/4828; G01R 33/5615
(Continued)

(56) References Cited

U.S. PATENT DOCUMENTS 5,909,119 A * 6/1999 Zhang ................ G01R 33/4828
324/307
6,016,057 A    1/2000 Ma
(Continued)

FOREIGN PATENT DOCUMENTS

WO    2009128764 A1    10/2009

OTHER PUBLICATIONS

Xiang, Q.S, "Two-Point Water-Fat Imaging with Partially-Opposed Phase (POP) Acquisition: An Asymmetric Dixon Method", Magnetic Resonance in Medicine 56:572-584 (2006).*
(Continued)

*Primary Examiner* — Mohamed Charioui
*Assistant Examiner* — Catherine Rastovski

(57) ABSTRACT

At least two chemical species are imaged using magnetic resonance imaging with signal separation for two chemical species resulting in separate signal datasets for these two chemical species. First and second echo data are acquired at different echo times resulting in a first and second acquired complex dataset. The first and second acquired datasets are modelled by employing a spectral signal model of at least one of the chemical species. The modelling results in a first and second modelled complex dataset. The first and second modelled datasets include a first and second phase error and the separate signal datasets for the two chemical species. From the first and second acquired dataset and the first and second modelled dataset the separate signal datasets for the two chemical species are determined.

18 Claims, 1 Drawing Sheet

(58) Field of Classification Search
USPC .......................................................... 702/22
See application file for complete search history.

(56) References Cited

U.S. PATENT DOCUMENTS

| | | | | |
|---|---|---|---|---|
| 6,106,057 | A * | 8/2000 | Lee | A47C 7/744 297/180.14 |
| 6,263,228 | B1 * | 7/2001 | Zhang | G01R 33/4828 128/899 |
| 6,603,990 | B2 * | 8/2003 | Zhang | A61B 5/055 324/307 |
| 7,099,499 | B2 * | 8/2006 | Blezek | G01R 33/4828 382/128 |
| 7,141,972 | B2 * | 11/2006 | Avram | G01R 33/4828 324/307 |
| 7,202,665 | B1 * | 4/2007 | Reeder | G01R 33/4824 324/307 |
| 7,619,411 | B2 | 11/2009 | Reeder | |
| 2005/0085713 | A1 * | 4/2005 | Reeder | A61B 5/055 600/422 |
| 2008/0048657 | A1 | 2/2008 | Reeder | |
| 2011/0140696 | A1 * | 6/2011 | Yu | G01R 33/4828 324/309 |
| 2012/0008847 | A1 | 1/2012 | Brendel et al. | |

OTHER PUBLICATIONS

Yu et al., "Multi-Echo Water-Fat Separation and Simultaneous R2 Estimation with Multi-Frequency Fat Spectrum Modeling", Magn. Reson. Med. 60(5) pp. 1122-1134, (2008).*

An, L., et al.; Chemical Shift Imaging with Spectrum Modeling; 2001; MRM; 46:126-130.

Ma, J.; Breath-Hold Water and Fat Imaging Using a Dual-Echo Two-Point Dixon Technique with an Efficient and Robust Phase-Correction Algorithm; 2004; MRM; 52:415-419.

Schmidt, M. A., et al.; Two-Point Dixon Fat-Water Separation: Improving Reliability and Accuracy in Phase Correction Algorithms; 2008; Journal of Magnetic Resonance Imaging; 27:1122-1129.

Xiang, Q-S.; Two-Point Water-Fat Imaging with Partially-Opposed-Phase (POP) Acquisition: An Asymmetric Dixon Method; 2006; MRM; 56:572-584.

Yu, H., et al.; Multiecho Water-Fat Separation and Simultaneous R2 Estimation with Multifrequency Fat Spectrum Modeling; 2008; MRM; 60:1122-1134.

* cited by examiner

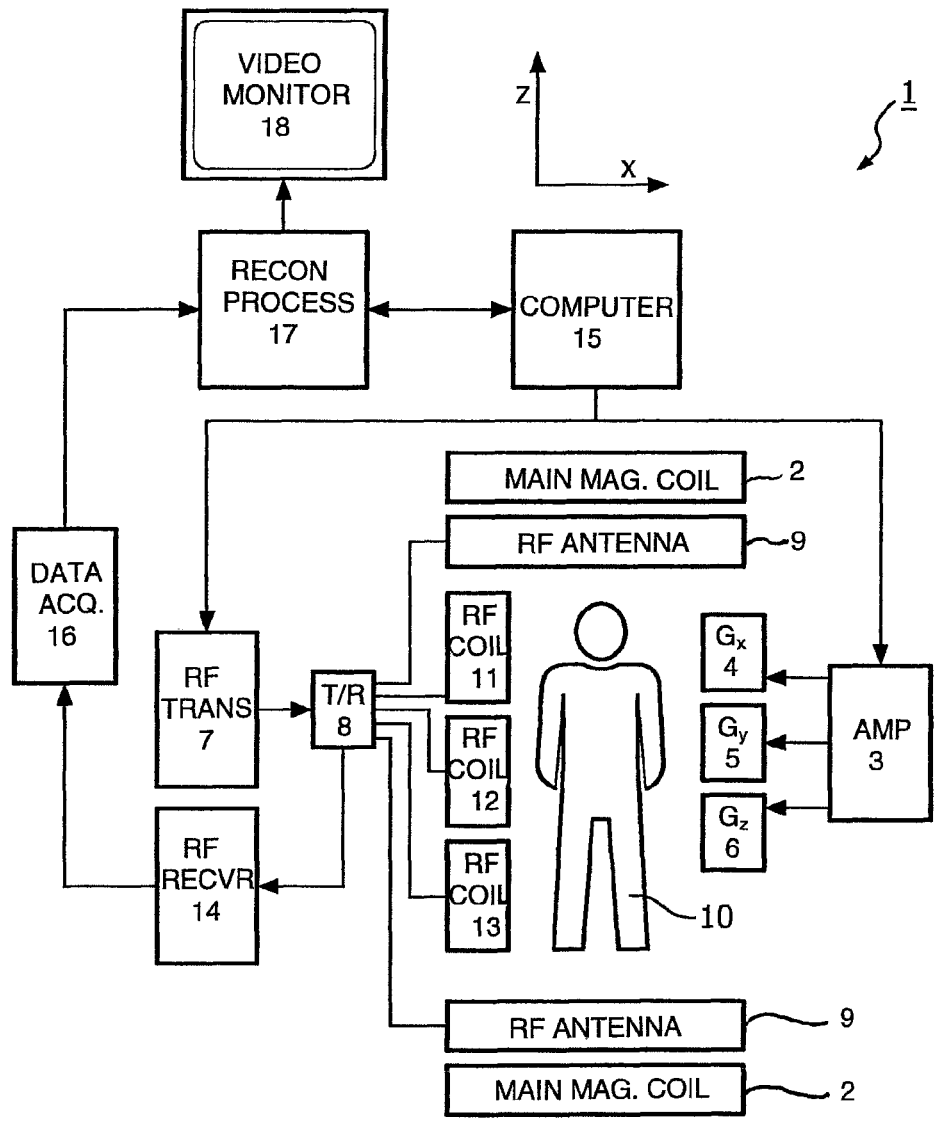

MAGNETIC RESONANCE IMAGING OF CHEMICAL SPECIES WITH A SPECTRAL MODEL

FIELD OF THE INVENTION

The invention relates to a method of imaging at least two chemical species using magnetic resonance imaging with signal separation for two chemical species, a computer program product and a magnetic resonance imaging apparatus for imaging at least two chemical species.

BACKGROUND OF THE INVENTION

Image-forming MR methods which utilize the interaction between magnetic field and nuclear spins in order to form two-dimensional or three-dimensional images are widely used nowadays, notably in the field of medical diagnostics, because for the imaging of soft tissue they are superior to other imaging methods in many respects, they do not require ionizing radiation, and they are usually not invasive.

According to the MR method in general, the body of a patient or in general an object to be examined is arranged in a strong, uniform magnetic field $B_0$ whose direction at the same time defines an axis, normally the z-axis, of the coordinate system on which the measurement is based.

The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a precessional motion about the z-axis.

Any variation of the magnetization can be detected by means of receiving RF antennas, which are arranged and oriented within an examination volume of the MR device in such a manner that the variation of the magnetization is measured in the direction perpendicularly to the z-axis.

In order to realize spatial resolution in the body, constant magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body.

The signal data obtained via the receiving antennas corresponds to the spatial frequency domain and is called k-space data. The k-space data usually includes multiple lines acquired with different phase encoding. Each line is digitized by collecting a number of samples. A set of samples of k-space data is converted to an MR image, e.g. by means of Fourier transformation.

In MRI, it often is desired to obtain information about the relative contribution of two dominant chemical species, such as water and fat, to the overall signal, either to suppress the contribution of one of them or to separately or jointly analyze the contribution of both of them. These contributions can be calculated if information from two or more corresponding echoes, acquired at different echo times, is combined.

A way to obtain information on water and fat contributions to the MR signal at the same time is chemical shift encoding, in which an additional dimension, the chemical shift dimension, is defined and encoded by acquiring a couple of images at slightly different echo times.

In particular for water-fat separation, these types of experiments are often called Dixon-type of measurements. By means of Dixon imaging or Dixon water/fat imaging, a water-fat separation can be obtained by calculating contributions of water and fat from two or more corresponding echoes, acquired at different echo times. Dixon imaging usually relies on the acquisition of at least two echoes to separate water and fat signals. In general these kinds of separations are possible because there is a known precessional frequency difference of hydrogen in fat and water. In its simplest form, water and fat images are generated by either addition or subtraction of the 'in phase' and 'out of phase' datasets, but this approach is rather sensitive to main field inhomogeneities.

High quality water-fat separation with no residual fat signal in water images may be obtained in case complex models of the fat spectrum are incorporated into the water-fat separation process. This has for example been demonstrated for three-point Dixon methods in Yu H, Shimakawa A, McKenzie C A, Brodsky E, Brittain J H, Reeder S B. Multi-echo water-fat separation and simultaneous R2* estimation with multi-frequency fat spectrum modeling. Magn Reson Med 2008; 60:1122-1134.

In particular in time critical applications such as abdominal imaging in a single breath hold, two-point methods are preferably used to reduce scan times as much as possible. However, they approximate the fat spectrum by a single, dominant peak and thus in general fail to provide a more efficient fat suppression. Moreover, the quality of the fat suppression depends strongly on the choice of echo times in the image data acquisitions.

SUMMARY OF THE INVENTION

From the foregoing it is readily appreciated that there is a need for an improved MR imaging method. It is consequently an object of the invention to enable MR imaging in a fast and reliable manner with high quality separation of two dominant chemical species in order to determine the relative contribution of said two dominant chemical species to an acquired overall signal.

In accordance with the invention, a method of imaging at least two chemical species using magnetic resonance imaging with signal separation for two chemical species resulting in separate signal datasets for these two chemical species is provided, wherein the method comprises acquiring first and second echo data at different echo times resulting in a first and second acquired complex dataset, modelling the first and second acquired dataset by employing a spectral signal model of at least one of the chemical species, said modelling resulting in a first and second modelled complex dataset, said first and second modelled dataset comprising a first and second phase error and the separate signal datasets for the two chemical species, determining from the first and second acquired dataset and the first and second modelled dataset the separate signal datasets for the two chemical species.

In other words, the present invention suggests an approach to incorporate more complex models of the spectrum of at least one of the chemical species into the separation of two-point methods. It thus permits enhancing the accuracy of a signal separation for the two chemical species and the efficiency of chemical species suppression.

It has to be noted here, that in case only one of the chemical species is modelled for example by a multi-peak spectral model, the other chemical species may simply be considered as a single line. Consequently, in fact both chemical species are modelled, wherein at least one of the models comprises a multi-peak spectral model.

Further, it has to be noted that the term 'chemical species' has to be broadly understood as any kind of predefined chemical substance or any kind of nuclei of predetermined magnetic resonance properties. In a simple example, the two chemical species are the protons in the 'chemical components' water and fat. In a more sophisticated example, a multi-peak spectral model actually describes a nuclei in a set of 'chemical components', which occur in known relative amounts. In this case, the multi-peak spectral models are introduced to separate two signal components, such as the products of a chemical reaction, for instance a metabolic process. Thus, the output of a certain metabolic process may be modelled in terms of output ratios for different products. These may then be combined into a single signal component, although they are different chemical species.

In accordance with an embodiment of the invention, the described datasets may be image space or k-space datasets. In case image datasets are preferred, the first and second echo data may be processed for reconstruction of the first and second acquired dataset, wherein the first and second acquired datasets are image datasets in this case.

In accordance with an embodiment of the invention, the determination of the separate signal datasets for the two chemical species is performed by minimizing the residuum between the first and second acquired and modelled datasets, where the latter are based on the spectral signal model of at least one of the chemical species. In the exemplary case of two chemical species, two complex equations, i.e. four total equations, are available, wherein the four unknowns in these four equations are the two separate signal datasets for the two chemical species and the first and second phase error. Consequently, by employing standard mathematical equation solving techniques including numerical techniques, from these four nonlinear equations the two separate signal datasets for the two chemical species can be obtained.

In accordance with a further embodiment of the invention, the determination of the separate signal datasets for the two chemical species comprises:

determining the magnitude of the first and second acquired dataset and retrieving an initial estimate of the separate signal datasets for the two chemical species based on the first and second modelled dataset, deriving from the first and second acquired dataset and the initial estimate of the separate signal datasets for the two chemical species at least one solution for the difference between the first and the second phase error based on the first and second modelled dataset, determining from the first and second acquired dataset and one solution for the difference between the first and the second phase error the final estimate of the separate signal datasets for the two chemical species.

This further simplifies the mathematical process of deriving the first and second phase error and the separate signal datasets for the two chemical species.

In accordance with an embodiment of the invention, the determination of the final estimate of the separate signal datasets for the two chemical species involves solving a system of two complex equations for two complex separate signals for the two chemical species.

In accordance with a further embodiment of the invention, the initial estimation of the separate signal datasets for the two chemical species comprises solving a system of two quadratic equations formed by the magnitude of the first and second acquired and modelled complex datasets. For example, this may be performed employing a biquadratic equation which permits to perform the retrieval of the separate signal datasets in a mathematically simple and thus fast manner. This further permits to speed up the signal separation process for the two chemical species.

In accordance with a further embodiment of the invention, the determination of the difference between the first and the second phase error results in a true and a false solution, wherein the method further comprises determining the true solution for example based on the assumption of smooth spatial variation of the main field inhomogeneities. In general, for the selection of the correct phasor value, any of a number of known methods, such as the regional iterative phasor extraction (RIPE), may be applied (compare for example Xiang Q S. Two-point water-fat imaging with partially-opposed-phase (POP) acquisition: an asymmetric Dixon method. Magn Reson Med 2006; 56:572-584).

It has to be noted, that throughout the description a phase error is understood either as an error of a phase itself, as well as an error of the respective phasor associated with a given phase.

In accordance with a further embodiment of the invention, the modelling of the first and second dataset comprises employing a linear combination of the separate signal datasets for the two chemical species, multiplied by a first and second phasor, the first and second phasor comprising the first and second phase error, wherein the weights for the linear combination are derived from the spectral signal model of the chemical species.

This type of modelling has the advantage that the separate signal datasets for the two chemical species can be obtained from just two different images, none of which needs to be in phase. Consequently, less restrictive assumptions regarding a Dixon reconstruction process need to be applied which enhances the quality of the reconstructed separate signal datasets for the two chemical species.

In accordance with a further embodiment of the invention, the determination of the separate signal datasets for the two chemical species is performed using the first and second magnitude, as well as the conjugate complex product of the two acquired datasets. Alternatively, a linear system of two equations may be solved by solely employing the first and second acquired dataset and the difference in the first and second phase error, i.e. without using the first and second magnitude. Since solving a linear system of two equations can be performed in a rather fast manner, a respective reconstruction process is further sped up. In addition, this approach adds one degree of freedom to the solution, which may help to reduce artifacts.

In accordance with a further embodiment of the invention, the two chemical species are water and fat. In this case, the spectral signal model is a multi-peak spectral model of fat. Consequently the present invention does not simply assume that only one dominant spectral peak of fat is present in the spectrum but rather employs a multi-peak spectral model of fat. In case only one of the chemical species, for example fat, is modelled, water may be considered as a single-peak spectrum.

Consequently it is assumed that for one of the species, for example fat, the relative resonance frequencies and the relative resonance strengths are known in advance, e.g. obtained from a theoretical or experimental model, or from a separate or integrated calibration, e.g. based on an identification of pixels that likely contain one chemical species like fat only.

In accordance with a further embodiment of the invention, the first and second phase error of the first and second acquired dataset comprises a phase error of the first and second image dataset excluding a chemical shift induced phase error due to the presence of said chemical species modelled by the spectral signal dataset model, i.e. for example excluding a chemical shift induced phase error due to the presence of fat.

The method of the invention can be advantageously carried out in most MR devices in clinical use at present. To this end, it is merely necessary to utilize a computer program by which the MR device is controlled such that it performs the above explained method steps of the invention. The computer program may be present either on a data carrier or be present in a data network so as to be downloaded for installation in the control unit of the MR device. Therefore, the invention also relates to a computer program product comprising computer executable instructions to perform the method as described above.

Further, the invention relates to a magnetic resonance imaging apparatus for imaging at least two chemical species, the apparatus comprising a magnetic resonance imaging scanner for acquiring magnetic resonance image data, the scanner being operable for:

acquiring first and second echo data at different echo times resulting in a first and second acquired complex dataset, modelling the first and second acquired dataset by employing a spectral signal model of at least one of the chemical species, said modelling resulting in a first and second modelled complex dataset, said first and second modelled dataset comprising a first and second phase error and separate signal datasets for the two chemical species, determining from the first and second acquired dataset and the first and second modelled dataset the separate signal datasets for the two chemical species.

BRIEF DESCRIPTION OF THE DRAWINGS

The enclosed drawing discloses a preferred embodiment of the present invention. It should be understood, however, that the drawing is designed for the purpose of illustration only and not as a definition of the limits of the invention.

DETAILED DESCRIPTION OF EMBODIMENTS

With reference to FIG. 1, an MR imaging system 1 is shown. The system comprises superconducting or resistive main magnet coils 2 such that a substantially uniform, temporarily constant main magnetic field $B_0$ is created along a z-axis through an examination volume.

A magnetic resonance generation manipulation system applies a series of RF pulses and switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier 3 applies current pulses to selected ones of whole body gradient coils 4, 5 and 6 along x, y and z-axes of the examination volume. An RF transmitter 7 transmits RF pulses or pulse packets, via a send/receive switch 8 to an RF antenna 9 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals may also be picked up by the RF antenna 9.

For generation of MR images of limited regions of the body or in general object 10, for example by means of parallel imaging, a set of local array RF coils 11, 12 and 13 are placed contiguous to the region selected for imaging. The array coils 11, 12 and 13 can be used to receive MR signals induced by RF transmissions effected via the RF antenna. However, it is also possible to use the array coils 11, 12 and 13 to transmit RF signals to the examination volume.

The resultant MR signals are picked up by the RF antenna 9 and/or by the array of RF coils 11, 12 and 13 and are demodulated by a receiver 14 preferably including a preamplifier (not shown). The receiver 14 is connected to the RF coils 9, 11, 12 and 13 via a send/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging and the like. For the selected sequence, the receiver 14 receives a single or a plurality of MR data lines in a rapid succession following each RF excitation pulse. A data acquisition system 16 performs analogue to digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, like for example Dixon reconstruction. The MR image may represent a planar slice through the patient, an array of parallel planar slices, a three-dimensional volume or the like. The image is then stored in an image memory where it may be accessed for converting slices or other portions of the image representation into appropriate formats for visualization, for example via a video monitor 18 which provides a man readable display of the resultant MR image.

In the following, an exemplary image reconstruction process employing the above described method shall be described in greater detail. The following procedure is proposed to consider a multi-peak spectral model of fat in the separation of a generic two-point method that does not impose any substantial constraints on the choice of the echo times.

The method starts with the acquisition of first and second echo data at different echo times $TE_n$, with n=1, 2, and a processing of said first and second echo data for reconstruction of a first and second image dataset $S_n$ by the reconstruction processor 17. Then, the composite complex signal S in image space for echo time $TE_n$, with n=1, 2, is modeled by:

$$S_n = (W + c'_n F) e^{i\phi_n}, \qquad (1)$$

where W and F denote the either real or complex water and fat signal in image space, $\phi_n$ denotes the phase errors, and $e^{i\phi_n}$ denotes the corresponding phasors. As mentioned above, the phase errors include the phase due to the main field inhomogeneities and a static phase that may arise from RF penetration and signal delay in the receiver chain excluding a chemical shift induced phase due to the presence of fat.

The spectral signal model of fat is provided via the complex weighting coefficients (i.e. complex factors) c' given by:

$$c'_n = \sum_m w_m e^{i\phi_{n,m}}, \quad (2)$$

where w denotes weights that add up to one and $\phi_{n,m}$ equals $2\pi \Delta f_m TE_n$, with $\Delta f_m$ being the offset in resonance frequency of the m-th peak of the fat spectrum with respect to water. Optionally, the influence of transverse relaxation may be included by adding a factor that describes the exponential decay with $TE_n$. The weights, the chemical shifts, and optionally the relaxation rates are assumed to be known a priori, either theoretically or experimentally, for example by a separate calibration process on the acquired MR images themselves. In a subsequent step, two signal components are calculated from $S_1$ and $S_2$ pixel by pixel or voxel by voxel (3D pixel). This is performed by considering the two magnitudes of the acquired and the modelled image datasets obtained from Eq. (1):

$$|S_1|^2 = w^2 + 2c'_{1R}WF + (c'^2_{1R} + c'^2_{1I})F^2, \quad (3)$$

$$|S_2|^2 = w^2 + 2c'_{2R}WF + (c'^2_{2R} + c'^2_{2I})F^2, \quad (4)$$

Here, $c'_{nR}$ and $c'_{nI}$ denote the real and imaginary components of $c'_n$. By employing the biquadratic equation $$a_1 F^4 + a_2 F^2 + a_3 = 0, \quad (5)$$

the two solutions $F_{1,2}$ $$F_{1,2} = \sqrt{-\frac{a_2}{2a_1} \pm \sqrt{\frac{a_2^2}{4a_1^2} - \frac{a_3}{a_1}}}, \quad (6)$$

may be derived. The constants a are given by:

$$a_1 = \frac{(c'^2_{1R} - c'^2_{1I} - 2c'_{1R}c'_{2R} + c'^2_{2R} + c'^2_{2I})^2 + 4(c'_{1R} - c'_{2R})^2 c'^2_{1I}}{}, \quad (7)$$

$$a_2 = 2(c'^2_{1R} - c'^2_{1I} - 2c'_{1R}c'_{2R} + c'^2_{2R} + c'^2_{2I})(|S_1|^2 - |S_2|^2) - 4(c'_{1R} - c'_{2R})^2 |S_1|^2, \quad (8)$$

$$a_3 = (|S_1|^2 - |S_1|^2)^2. \quad (9)$$

The corresponding two solutions for $W_{1,2}$ are:

$$W_{1,2} = -c'_{1R}F \pm \sqrt{|S_2|^2 - c'^2_{1I}F^2}. \quad (10)$$

Consequently, a first and second species specific image dataset W and F can be obtained from said magnitudes calculated in Eqs. (3) and (4).

From the model of the first and second modelled image dataset Eq. (1) and the two pairs of values for W and F (Eqs. 6 and 10), two values for the phasor $\Delta P_{1,2} = e^{i(\Phi_2 - 100_1)}$ are obtained:

$$\Delta P_{1,2} = \frac{S_1^* S_2}{(W_{1,2} + c'^*_1 F_{1,2})(W_{1,2} + c'_2 F_{1,2})}. \quad (11)$$

This results in two possible phasor candidates, one being true and one being false. The true phasor is extracted from the two phasor candidates through a procedure such as the regional iterative phasor extraction (RIPE) procedure. Additionally, the estimate of the true phasor may be adapted in view of the results obtained in a spatial neighbourhood of the pixel.

Given the this estimate of the phasor, W and F are recalculated. This may, for instance, be done by solving a non-linear system of four equations for the real variables W and F, of which two are those for $|S_1|^2$ and $|S_1|^2$ in Eqs. (3) and (4) and two are the real and imaginary components of $$S_1^* S_2 \Delta P^* = (W + c'_1{}^* F)(W + c'_2 F). \quad (12)$$

Alternatively, a linear system of two equations may be solved for the complex variables W' and F':

$$S_1 = W' + c'_1{}^* F', \quad (13)$$

$$S_2 \Delta P^* = W' + c'_2 F'. \quad (14)$$

Since $W' = We^{i\Phi_1}$ and $F' = Fe^{i\Phi_1}$, the magnitude of W' and F' is equal to that of W and F.

Consequently, by carrying out the above described steps by the reconstruction processor 17, a good water-fat separation is achieved with a fast data acquisition method. Water and fat can be separated from just two complex valued images, none of which needs to be in phase.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of imaging at least two chemical species using magnetic resonance imaging with signal separation for two chemical species resulting in separate signal datasets for these two chemical species, the method comprising:

acquiring first and second echo data at two different echo times using a two-point method resulting in a first and second acquired complex datasets, modelling the first and second acquired complex datasets by multi-peak model of at least one of the chemical species said modelling resulting in a first and second modelled complex dataset, said first and second modelled complex datasets comprising a first and second phasor and separate signal complex datasets for the two chemical species, the modelling of the first and second complex datasets employing a linear combination of the separate signal complex datasets for the two chemical species, multiplied by the first and second phasor, weights for the linear combination being derived from the spectral signal model of at least one of the chemical species;

determining the magnitude of the first and second acquired complex datasets and retrieving an initial estimate of the separate signal datasets for the two chemical species based on the first and second modelled complex datasets, deriving from the first and second acquired complex datasets and the initial estimate of the separate signal datasets for the two chemical species at least one solution for the first and second phasors based on the first and second modelled complex datasets, determining from the first and second acquired complex datasets and one solution for the first and second phasors a final estimate of the separate signal complex datasets for the two chemical species by minimizing a residuum between the first and second acquired complex datasets and the first and second modelled complex datasets, reconstructing at least one of the first and second species datasets into an image, and, displaying at least one of the images on a display device.

2. The method of claim 1, wherein the initial estimation of the separate signal complex datasets for the two chemical species comprises solving a system of two quadratic equations formed by a magnitude of the first and second acquired and modelled complex datasets.

3. The method of claim 2, wherein the system of two quadratic equations is analytically solved by deriving a biquadratic equation.

4. The method of claim 1, wherein the determination of the first and second phasors results in a true and a false solution, wherein the method further comprises determining the true solution based on a spatial smoothness assumption of main field inhomogeneities.

5. The method of claim 4, wherein determining the true solution is performed with a regional iterative phasor extraction process.

6. The method of claim 1, wherein the two chemical species are water and fat and the spectral signal model is a multi-peak spectral model of fat.

7. The method of claim 1, wherein the determination of the final estimate of the separate signal complex datasets for the two chemical species involves solving a system of two complex equations for two complex separate signals for the two chemical species.

8. A non-transitory computer-readable medium carrying computer executable instructions to control a computer to perform the method as claimed in claim 1.

9. A magnetic resonance imaging apparatus for imaging at least first and second chemical species, the apparatus comprising a magnetic resonance imaging scanner for acquiring magnetic resonance image data, the scanner being operable for:

acquiring first and second echo data at two different echo times employing a two-point DIXON acquisition resulting in a first acquired complex dataset and a second acquired complex dataset, modelling the first acquired complex dataset and second acquired complex dataset by employing a spectral signal model of at least one of the chemical species, said modelling resulting in a first modelled complex dataset and a second modelled complex dataset, said first modelled complex dataset and the second modelled complex dataset having a first phasor and a second phasor and separate signal datasets for the first and second chemical species, the modelling of the first acquired complex data set and the second acquired complex dataset employing a linear combination of the separate first and second acquired complex datasets for the two chemical species multiplied by the first phasor and the second phasor, respectively, weights for the linear combination being derived from the spectral signal model of at least one of the first and second chemical species;

determining the magnitude of the first and second acquired complex datasets and retrieving an initial estimate of the separate first and second acquired complex datasets for the two chemical species based on the first and second modelled complex datasets;

deriving from the first and second acquired complex datasets and the initial estimate of the first and second complex datasets for the two chemical species at least one solution for the first and second phasors based on the first and second modelled complex datasets;

determining from the first and second acquired complex datasets and one solution for the first and second phasors a final estimate of separate first and second signal complex datasets for the two chemical species;

reconstructing at least one of the separate first and second complex datasets into an image, and displaying at least one of the images on a display device.

10. The method of claim 1, wherein the first and second acquired complex datasets are k-space datasets, the first and second modelled complex datasets are first and second complex modelled k-space datasets and, the separate complex signal datasets include a first species k-space dataset and a second species k-space dataset, and further including:

reconstructing at least one of the first and second species k-space datasets into at least one of a first species image and a second species image; and displaying at least one of the first species image and the second species on a display device.

11. The magnetic resonance imaging apparatus of claim 9, wherein the first and second acquired complex datasets are first and second acquired complex k-space datasets, the first and second modelled complex datasets are first and second modelled k-space complex datasets and, the separate signal complex datasets include a first species k-space dataset and a second species k-space dataset, and wherein the scanner is further operative for:

reconstructing at least one of the first and second k-space datasets into an image.

12. The magnetic resonance imaging apparatus of claim 9, wherein the two chemical species are water and fat, and the spectral model is a multi-peak spectral model of fat.

13. The method of claim 1, wherein the first and second acquired complex datasets are images reconstructed from the first and second echo data, respectively, the first and second modelled complex datasets are image datasets, and wherein the separate signal complex datasets include two images, each limited to one of the chemical species, and further including:

displaying at least one of the images on a display device.

14. The magnetic resonance imaging apparatus of claim 9, wherein the first and second acquired complex datasets are images reconstructed from the first and second echo data, respectively, and wherein the first and second modelled complex datasets are image datasets, and wherein the separate signal complex datasets include two images, each limited to one of the chemical species, and wherein the scanner is further operable for:

displaying at least one of the images on a display device.

15. A magnetic resonance imaging apparatus for generating an image of at least a single chemical species of an object including at least first and second chemical species, the imaging apparatus comprising:

at least one computer processor configured to:

using a two-point DIXON acquisition technique, receive first and second echo data generated at two different echo times from a magnetic resonance imaging scanner;

reconstruct the first and second echo data into first and second acquired image datasets, model the first and second acquired image datasets by employing a multi-peak spectral model of at least one of the two chemical species to generate first and second modelled image datasets and first and second phasors for the first and second chemical species, the modelling of the first and second acquired image datasets including linearly combining the first and second acquired image datasets for the two chemical species multiplied by the first and second phasors, weights for the linear combination being derived from the multi-peak spectral model of at least one of the first and second chemical species, determine a magnitude of the first and second acquired complex datasets and retrieve an initial estimate of the separate signal datasets for the two chemical species based on the first and second modelled complex datasets, derive from the first and second acquired complex datasets and the initial estimate of the separate signal datasets for the two chemical species at least one solution for the first and second phasors based on the first and second modelled complex datasets, minimize a residuum between the first and second acquired image datasets and the first and second modelled image datasets to generate a first chemical species image and a second chemical species image;

a display device configured to display at least one of the first and second species images.

16. The magnetic resonance imaging apparatus of claim 15, wherein the two chemical species are water and fat, and the multi-peak spectral model is of fat.

17. A magnetic resonance imaging apparatus for generating an image of at least a single chemical species of an object including at least first and second chemical species, the imaging apparatus comprising:

at least one computer processor configured to:

using a two-point acquisition technique, receive first and second echo data generated at only two different echo times from a magnetic resonance imaging scanner, the first echo data including first echo k-space data and the second echo data including second echo k-space data, model the first and second echo k-space data by employing a multi-peak spectral model of at least one of the two chemical species to generate first and second modelled k-space data and first and second phasors for the first and second chemical species, the modelling of the first and second echo k-space data including linearly combining the first and second k-space data multiplied by the first and second phasors, weights for the linear combination being derived from the multi-peak spectral signal model of at least one of the first and second chemical species, minimize a residuum between the first and second echo k-space data and the first and second modelled k-space data to generate first chemical species k-space data and a second chemical species k-space data, determine a magnitude of the first and second acquired complex datasets and retrieve an initial estimate of the separate signal datasets for the two chemical species based on the first and second modelled complex datasets, derive from the first and second acquired complex datasets and the initial estimate of the separate signal datasets for the two chemical species at least one solution for the first and second phasors based on the first and second modelled complex datasets, reconstruct at least one of the first and second species k-space data into an image;

a display device configured to display the at least one image.

18. The magnetic resonance imaging apparatus of claim 17, wherein the two chemical species are water and fat, and the multi-peak spectral model is of fat.

* * * * *